(12) United States Patent
Bernardino (10) Patent No.: US 8,350,086 B2
(45) Date of Patent: Jan. 8, 2013

(54) PROCESS FOR PREPARING CINACALCET HYDROCHLORIDE

(75) Inventor: Mangion Bernardino, Santa Lucia (MT)

(73) Assignee: Medichem, S.A., Barcelona (ES)

( * ) Notice: Subject to any disclaimer, the term of this patent is extended or adjusted under 35 U.S.C. 154(b) by 259 days.

(21) Appl. No.: 12/678,971

(22) PCT Filed: Sep. 18, 2008

(86) PCT No.: PCT/US2008/076793
§ 371 (c)(1),
(2), (4) Date: Jul. 23, 2010

(87) PCT Pub. No.: WO2009/039241
PCT Pub. Date: Mar. 26, 2009

(65) Prior Publication Data
US 2010/0298606 A1    Nov. 25, 2010

Related U.S. Application Data

(60) Provisional application No. 60/960,155, filed on Sep. 18, 2007, provisional application No. 61/064,525, filed on Mar. 10, 2008.

(51) Int. Cl.
*C07C 211/00* (2006.01)
(52) U.S. Cl. ...................................................... 564/374
(58) Field of Classification Search .................... 564/374
See application file for complete search history.

(56) References Cited

FOREIGN PATENT DOCUMENTS

| WO | 2006/127932 | 11/2006 |
|---|---|---|
| WO | 2008/058235 | 5/2008 |
| WO | 2008/058236 | 5/2008 |

OTHER PUBLICATIONS

May 14, 2009 PCT/US2008/076793 International Search Report.

*Primary Examiner* — Rebecca Anderson
*Assistant Examiner* — Samantha Shterengarts
(74) *Attorney, Agent, or Firm* — Cozen O'Connor (57) ABSTRACT

The invention relates to an improved process for preparing cinacalcet hydrochloride. The invention provides an efficient and economic process for preparing cinacalcet hydrochloride which is suitable for industrial implementation i.e., affords cinacalcet hydrochloride with high purity, and uses small volumes of acidifying agent and solvents. The invention also related to a process for preparing a cinacalcet carboxylate salt, including cinacalcet accetate

25 Claims, 9 Drawing Sheets

Figure 1A  IR spectrum of cinacalcet base

Figure 1B   IR spectrum of cinacalcet base (evaporated film on NaCl plate)

Figure 2 IR Spectrum of cinacalcet acetate

Figure 3  IR spectrum of cinacalcet hydrochloride

Figure 4 IR spectrum of cinacalcet acetate (KBr disc)

Figure 5 $^1$H-NMR spectrum of cinacalcet acetate (CDCl$_3$)

Figure 6 IR spectrum of cinacalcet hydrochloride (KBr disc)

Figure 7 XRD spectrum of cinacalcet acetate

Figure 8 $^1$H-NMR spectrum of cinacalcet base (CDCl$_3$)

PROCESS FOR PREPARING CINACALCET HYDROCHLORIDE

CROSS REFERENCE TO RELATED APPLICATIONS

This application is a national stage application under 35 U.S.C. §371 of International Application No. PCT/US2008/076793, filed Sep. 18, 2008, which claims priority to and the benefit of U.S. Provisional Application No. 60/960,155 filed Sep. 18, 2007, and U.S. Provisional Application No. 61/064,525, filed Mar. 10, 2008. The entire contents of each of the above-identified applications are hereby incorporated by reference herein.

BACKGROUND OF THE INVENTION

1. Field of the Invention

The invention relates to an improved process for preparing cinacalcet hydrochloride.

2. Related Art

Cinacalcet hydrochloride is a commercially marketed pharmaceutically active substance known to be useful for the treatment of hyperparathyroidism and the preservation of bone density in patients with kidney failure or hypercalcemia due to cancer. Cinacalcet hydrochloride is the generic international denomination for N-[1-(R)-(–)-(1-naphthyl)ethyl]-3-[3-(trifluoromethyl)phenyl]-1-aminopropane hydrochloride, which has the Formula (I) given below:

Formula I

Cinacalcet hydrochloride is an oral calcimimetic drug. In the United States, it is marketed under the name Sensipar® and, in Europe, it is marketed under the name Mimpara® and Parareg®. It has been approved for the treatment of secondary hyperparathyroidism in patients with chronic kidney disease on dialysis and for the treatment of hypercalcemia in patients with parathyroid carcinoma.

U.S. Pat. No. 6,011,068 generally describes cinacalcet and its pharmaceutically acceptable acid additions salts but does not provide any examples for the preparation of the same.

U.S. Pat. No. 6,211,244 describes cinacalcet and its pharmaceutically acceptable acid chloride addition salt but does not provide any examples for the preparation of cinacalcet and/or cinacalcet hydrochloride.

U.S. Pat. No. 7,247,751 discloses that the crystalline cinacalcet hydrochloride currently marketed as Sensipar® is characterized as crystalline Form I (denominated as Form I), and encompasses processes for its preparation. The examples provided, however, are not efficient for industrial implementation, i.e., do not specify the purity of the obtained cinacalcet hydrochloride, and use large volumes of acidifying agent and solvents.

International Patent Publication No. WO 2008/058236 provides additional processes for making cinacalcet hydrochloride. Among others, Example 26 of International Patent Publication No. WO 2008/058236 describes the preparation of cinacalcet hydrochloride via treating cinacalcet acetate salt with hydrochloric acid.

There is therefore a need of providing an efficient and economic process for preparing cinacalcet hydrochloride be suitable for industrial implementation.

BRIEF DESCRIPTION OF THE DRAWING

The accompanying drawings, which are included to provide a further understanding of the invention and are incorporated in and constitute a part of this specification, illustrate embodiments of the invention and together with the description serves to explain the principles of the invention. In the drawings.

DETAILED DESCRIPTION OF THE PREFERRED EMBODIMENTS

The invention provides an efficient and economic process for preparing cinacalcet hydrochloride which is suitable for industrial implementation i.e., affords cinacalcet hydrochloride with high purity, and uses small volumes of acidifying agent and solvents. In particular, the invention provides a process for producing cinacalcet hydrochloride, said process including: (i) providing a cinacalcet carboxylate salt, and (ii) converting said cinacalcet carboxylate salt into cinacalcet hydrochloride by means of an anion exchange reaction.

In a preferred embodiment, the process of the invention is characterized in that the cinacalcet carboxylate salt is preferably a cinacalcet $C_{1-5}$ carboxylate salt, more preferably is cinacalcet acetate.

In another preferred embodiment, the process of the invention is characterized in that the step (i) of providing a cinacalcet carboxylate salt includes: (i) contacting cinacalcet free base with a carboxylic acid in a mixture of at least one organic solvent and water, (ii) removing the water from the mixture, and (iv) optionally, isolating cinacalcet carboxylate from the mixture.

The at least one organic solvent is preferably at least one of an alcohol solvent and an ester solvent, preferably is at least one of a $C_{1-5}$ alcohol solvent and an acetate ester solvent, more preferably is at least one of isopropanol and isobutyl acetate.

The carboxylic acid is preferably a $C_{1-5}$ carboxylic acid, more preferably is acetic acid.

In another preferred embodiment, the process of the invention is characterized in that the step (ii) of converting said cinacalcet carboxylate salt into cinacalcet hydrochloride by means of an anion exchange reaction, includes: (i) contacting said cinacalcet carboxylate salt with a compound donor of chloride ions in a mixture of at least one organic solvent and water, (ii) isolating cinacalcet hydrochloride from the mixture, and (iii) optionally, purifying said cinacalcet hydrochloride.

The at least one organic solvent is preferably at least one of an alcohol solvent and an ester solvent, preferably is at least one of a $C_{1-5}$ alcohol solvent and an acetate ester solvent, more preferably is at least one of isopropanol and isobutyl acetate.

The compound donor of chloride ions is preferably at least one of hydrogen chloride, hydrochloric acid, alkali metal chloride, and ammonium chloride, more preferably is at least one of hydrochloric acid and sodium chloride.

Another aspect of the invention includes the process of using a cinacalcet carboxylate salt for preparing cinacalcet hydrochloride, by means of an anion exchange reaction.

Figure 1A:
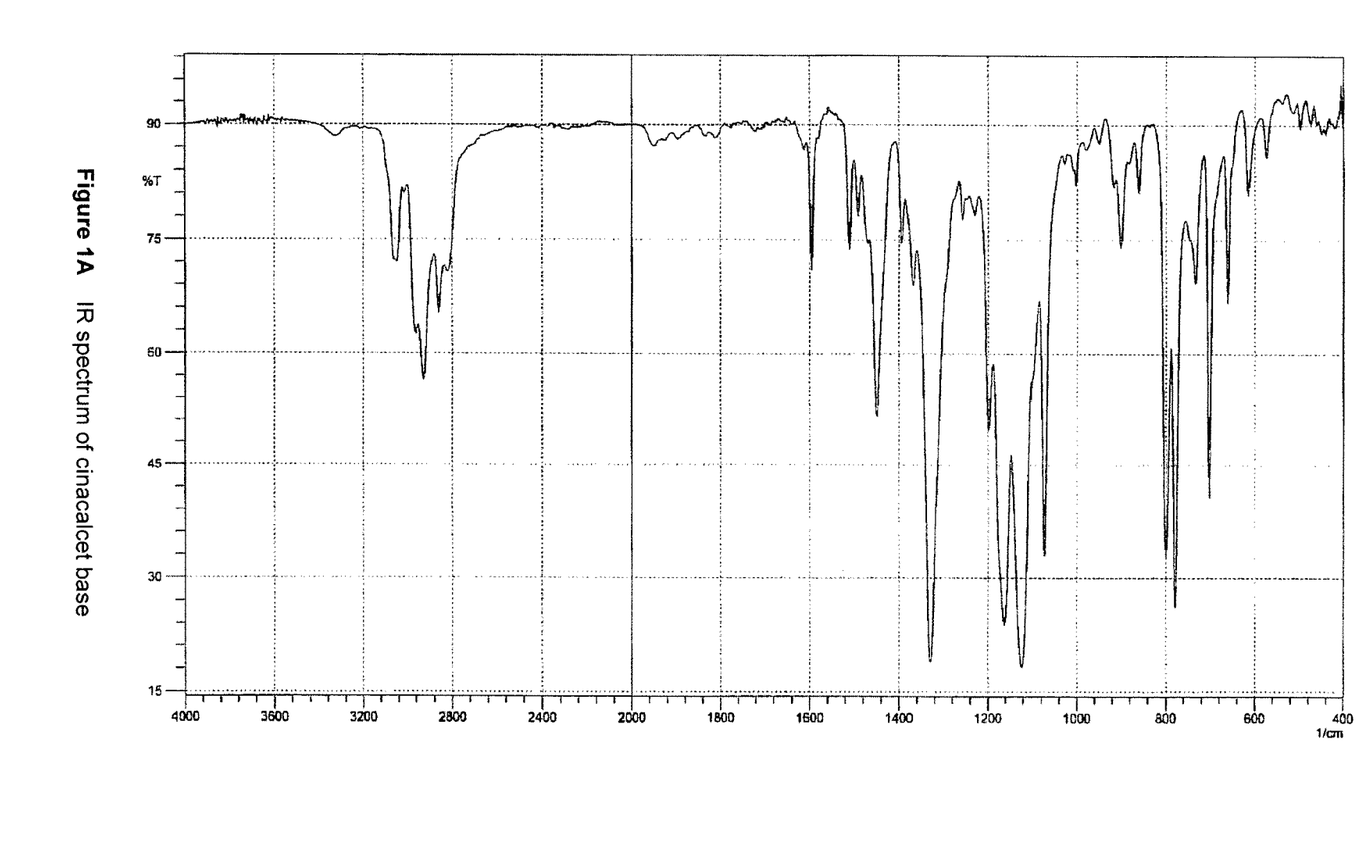
FIG. 1A illustrates the IR spectrum of cinacalcet base.
Figure 1B:
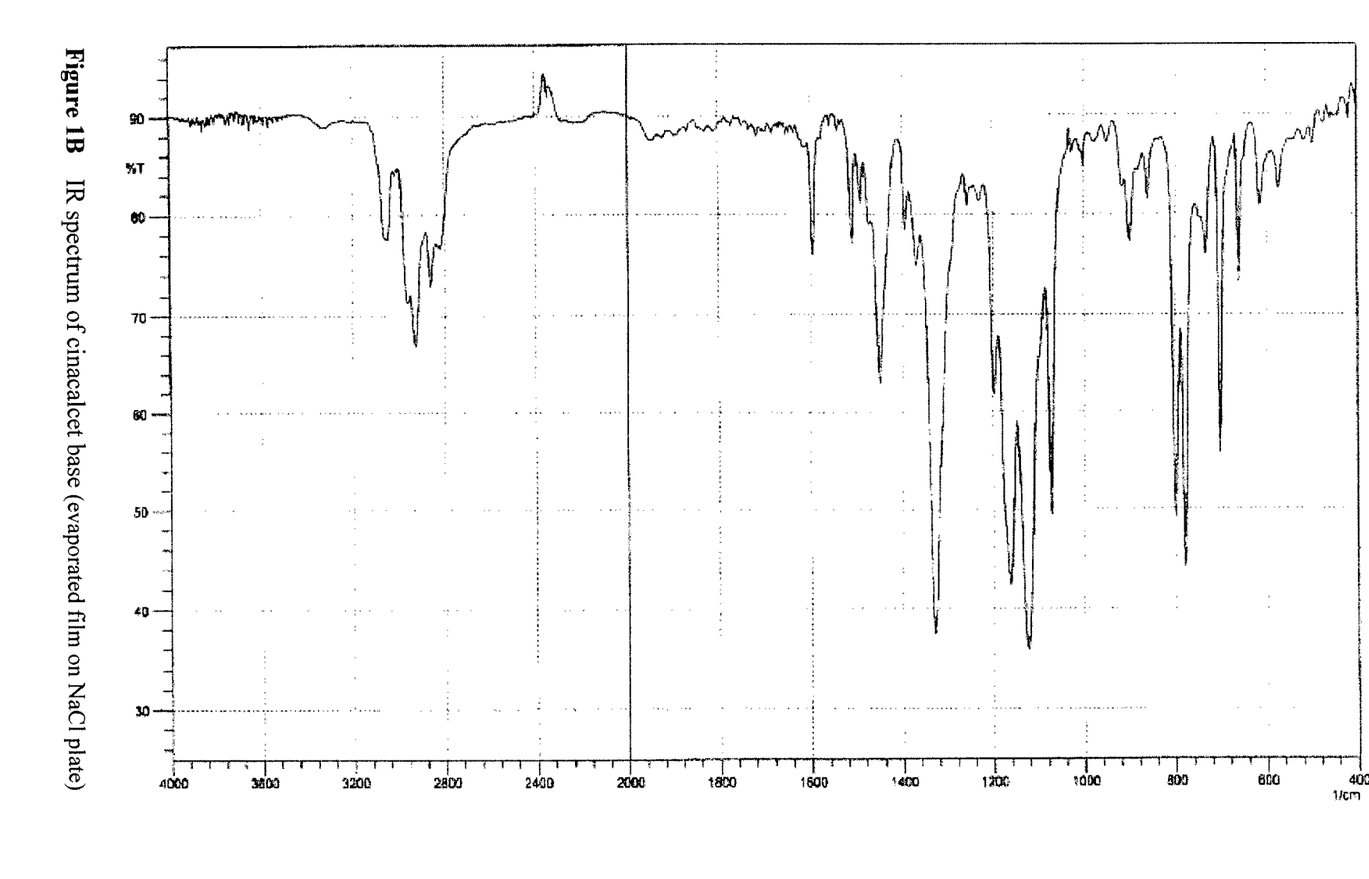
FIG. 1B illustrates the IR spectrum of cinacalcet base (NaCl plate)
Figure 2:
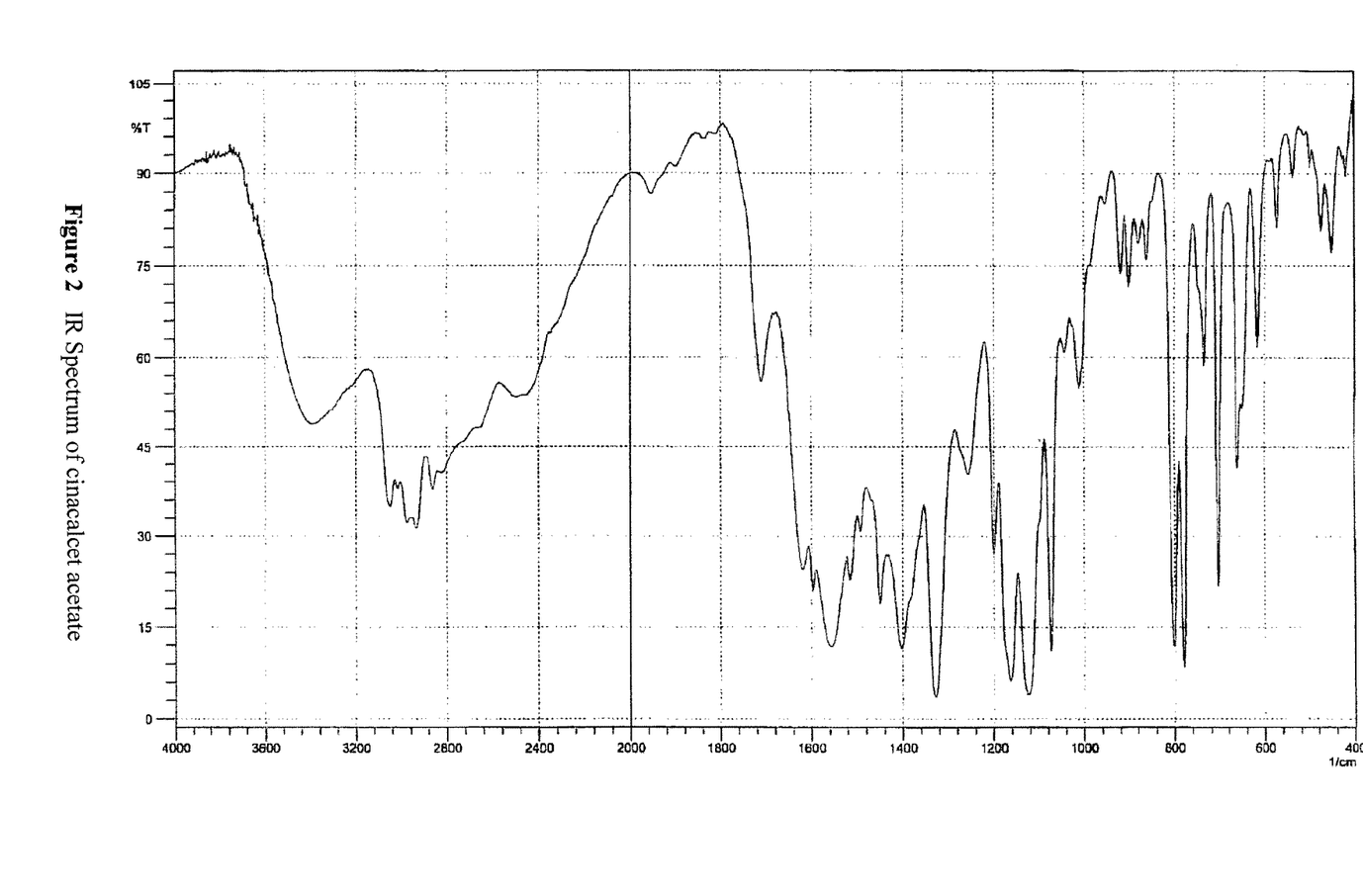
FIG. 2 illustrates the Infra Red of cinacalcet acetate.

Another aspect of the invention includes a new cinacalcet salt, i.e., cinacalcet acetate, which is characterized by its IR spectrum. FIG. 2 illustrates the IR spectrum of cinacalcet acetate.

Another aspect of the invention includes a process for producing cinacalcet acetate, said process includes: (i) contacting cinacalcet free base with acetic acid in a mixture of at least one organic solvent and water, (ii) removing the water from the mixture, and (iii) isolating cinacalcet acetate from the mixture.

The at least one organic solvent is preferably at least one of an alcohol solvent and an ester solvent, preferably is at least one of a $C_{1-5}$ alcohol solvent and an acetate ester solvent, more preferably is at least one of isopropanol and isobutyl acetate.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

General Experimental Conditions

HPLC Method

HPLCs were acquired on a Shimadzu Prominence LC-20 system. Column: Symmetry C8, 5 μm, 4.6×250 mm. Flow rate: 1 mL/min. Detector: UV, 270 nm. Mobile phase A: 40:60 20 mM ammonium formate, pH 7.0: acetonitrile. Mobile phase B: acetonitrile. Gradient: 100% A (0 minutes)-100% A (25 minutes)-35% A (35 minutes)-35% A (65 minutes)-100% A (70 minutes)-100% A (80 minutes). Temperature: ambient. Sample: 5 mg/mL in mobile phase A. Injection volume: 10 μL.

X-Ray Powder Diffraction (XRD)

XRD diffractograms were obtained using a RX SIEMENS D5000 diffractometer with a vertical goniometer, a copper anodic tube, and radiation $CuK_\alpha$, $\lambda=1,54056$ Å.

Fourier Transform Infrared (FT-IR)

FT-IR spectra were acquired on a Shimadzu FT-IR 8400S spectrophotometer.

Nuclear Magnetic Resonance (NMR)

$^1H$, $^{13}C$ and 2D NMR experiments were performed on a Varian Mercury 400 MHz spectrometer at room temperature.

Potentiometric Assay for Cinacalcet Hydrochloride 400 mg of sample were weighed accurately, dissolved in 60 mL of glacial acetic acid and 10 mL of 5% mercury (II) acetate, and were titrated immediately with 0.1 N HClO4 VS, determining the end-point potentiometrically. Each mL of 0.1 N HClO4 VS was equivalent to 39.387 mg of cinacalcet. Calculate with reference to the dry substance.

Example 1

Preparation of Cinacalcet Acetate from Cinacalcet Base

To a stirred solution of 1.50 g (4.20 mmol) cinacalcet base in 3 mL isopropanol at room temperature, 3.36 g (8.40 mmol) of 15% w/w aqueous acetic acid were added dropwise. n-Heptane (6 mL) was added and the organic phase was separated and evaporated to dryness to give a pale yellow oil. Isobutyl acetate (4.5 mL) and 3 mL of water were added onto the residue and the mixture was stirred for 15 minutes at room temperature. The phases were then separated. The organic phase was dried over anhydrous $MgSO_4$ and then evaporated to dryness to give 1.54 g of a yellow oil (Yield: 88.0%).

Assay ($HClO_4$): 94.4%; IR according to FIG. 2; $^1H$ NMR ($CDCl_3$, 400 MHz): δ 1.61 ppm (3H, d, $CH_3$ and NH), 1.91 ppm (2H, quin., $NHCH_2CH_2CH_2Ar$), 2.07 ppm (3H, s, acetate), 2.57-2.76 ppm (4H, m, $NHCH_2CH_2CH_2Ar$), 4.85 ppm (1H, distorted q, $CHCH_3$), 6.13 (broad s, $NH_2^+$), 7.24-8.12 ppm (11H, m, aromatic).

Example 2

Preparation of Cinacalcet Hydrochloride from Cinacalcet Acetate

To a stirred solution of 5.43 g (13.01 mmol) cinacalcet acetate, prepared as described in Example 1, in 27.31 g isobutyl acetate at room temperature, 17.82 g (32.26 mmol) of 10.58% w/w NaCl aqueous solution were added dropwise. The formation of white solid was quickly observed to give a thick suspension. The mixture was stirred at room temperature overnight, and the solid was filtered and washed with 6 mL of i-BuOAc to give 6.501 g of material (LOD: 38.20%, yield: 78.5%).

Next, 2.57 g of dry material were stirred with 4.5 volumes of water for 1 hour at room temperature. The suspension was then cooled down to 5-10° C. and stirred for 30 minutes. The suspension was filtered and washed with 2 mL of water to give 2.30 g of dry product (LOD: 15.63%; yield: 89.4%).

The product was then dissolved in 9.2 mL of ethanol and filtered to remove insoluble particles and the solvent was then displaced using two 9.2 mL portions of isobutyl acetate and evaporated to dryness.

Figure 3:
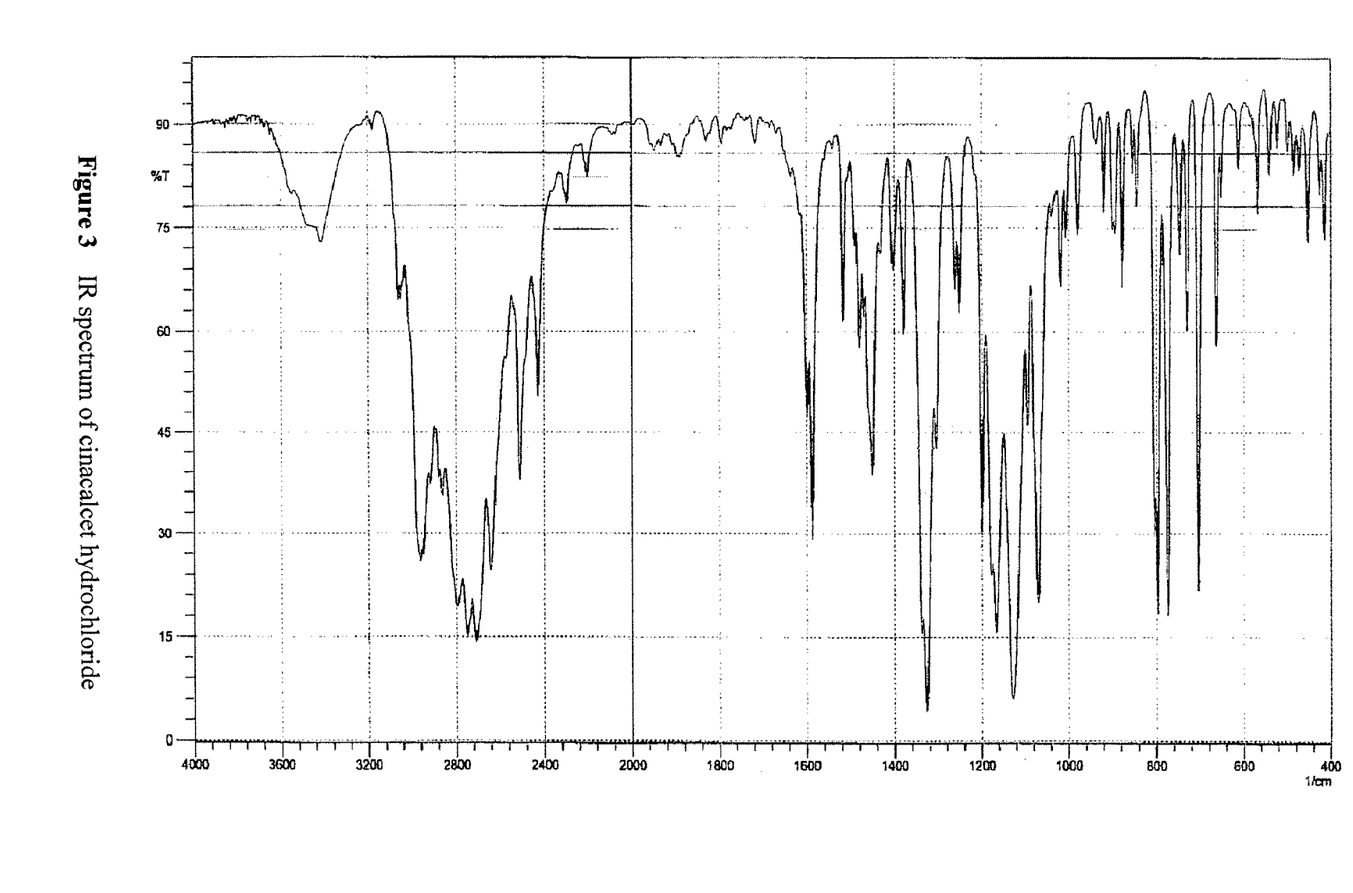
FIG. 3 illustrates the Infra Red spectrum of cinacalcet hydrochloride.

Finally, a crystallization was performed using 16 mL of isobutyl acetate. The solid was dried to give 2.05 g of cinacalcet hydrochloride (LOD: 0.55%, yield: 89.1%). Overall yield: 79.7%; Assay ($HClO_4$): 99.4%; Cl content: 9.01% (theoretical content: 9.01%); mp 179.5° C.-180.3° C.; IR according to FIG. 3.

Example 3

Preparation of Cinacalcet Acetate from Cinacalcet Base

To a stirred solution of 47.94 g (134.20 mmol) cinacalcet base and 96 mL isobutyl acetate at room temperature, 108.53 g (268.40 mmol) of 15% w/w aqueous acetic acid were added dropwise. The mixture was stirred at room temperature for 5.5 hours and then evaporated to dryness to give a yellow oil. This product was dissolved in 144 mL of isobutyl acetate and 96 mL of water were added. The mixture was stirred at room temperature for 30 minutes and then phases were separated. The organic phase was stirred at room temperature for 30 minutes with further 96 mL of water. The phases were then separated, the organic phase was dried over anhydrous $MgSO_4$ and evaporated to dryness to give a yellow solid. This solid was dried in a vacuum oven at 40° C. for 6 hours to yield 55.89 g of yellow solid (LOD: 1.11%, yield: 99.8%).

Figure 4:
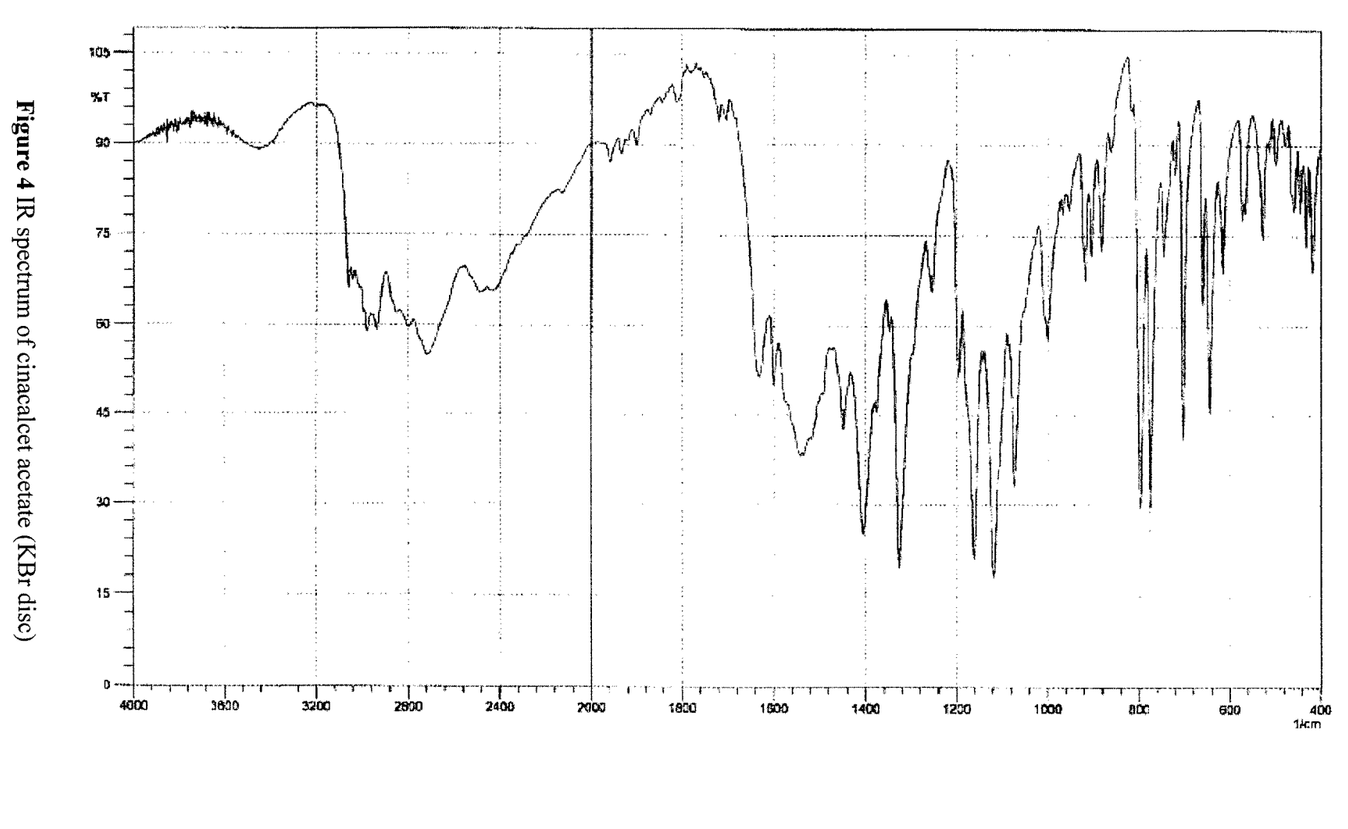
FIG. 4 illustrates the Infra Red spectrum of cinacalcet acetate (KBr disc)
Figure 5:
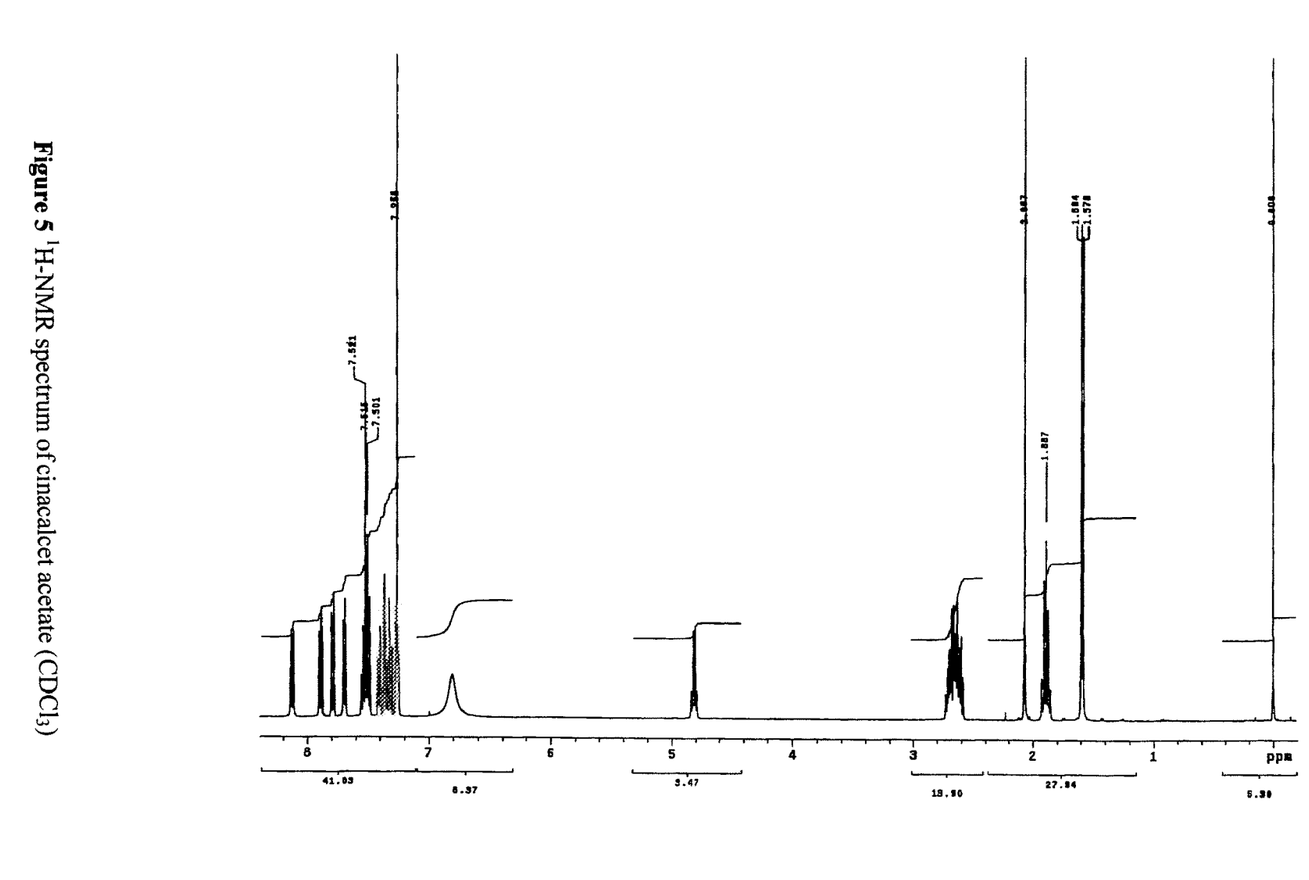
FIG. 5 illustrates the $^1$H-NMR spectrum of cinacalcet acetate (CDCl$_3$)
Figure 7:
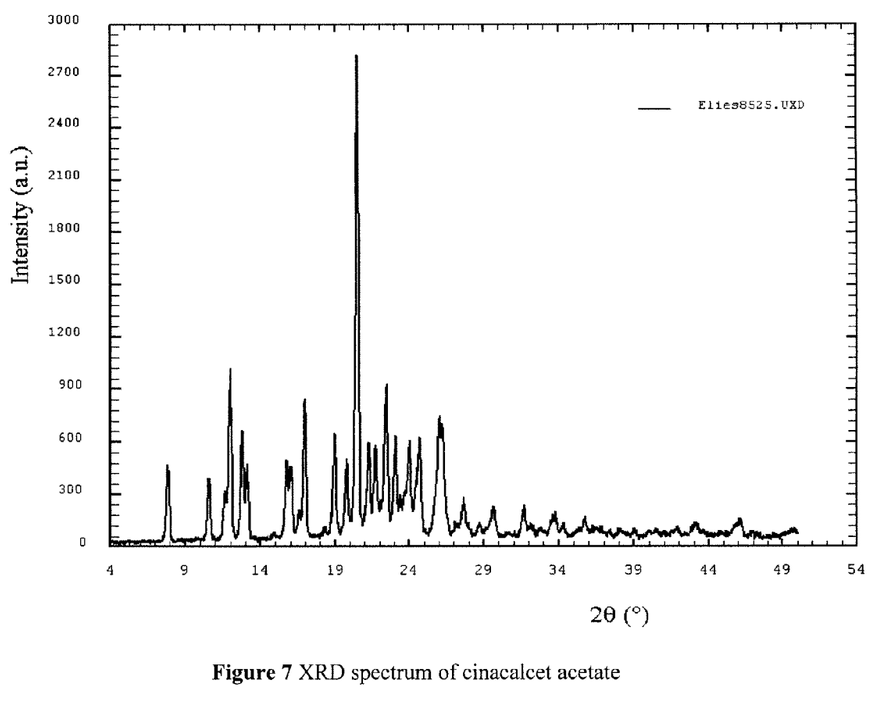
FIG. 7 illustrates the X-ray Diffraction spectrum of cinacalcet acetate.
Figure 8:
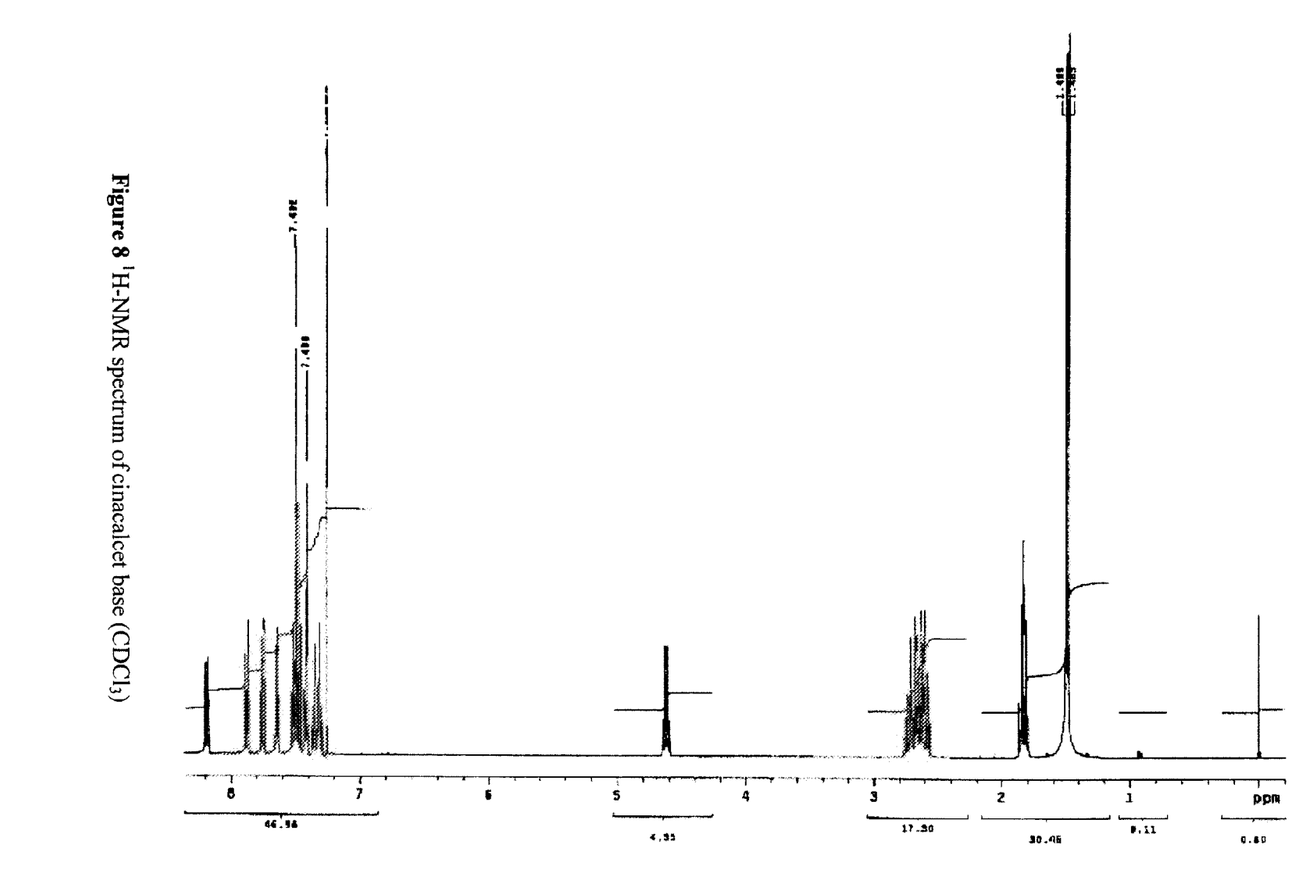
FIG. 8 illustrates the $^1$H-NMR spectrum of cinacalcet base (CDCl$_3$).

The following analyses of the dry solid were made: Cl content: 0%; Optical rotation $[\alpha]_D^{20}$: −15.8° (C=2, MeOH); HPLC: 99.85% (% area); IR according to FIG. 4; $^1$H NMR ($CDCl_3$, 400 MHz): 1.59 (3H, d, J=6.4 Hz, $CHCH_3$), 1.89 (2H, quint., J=7.5 Hz, $NHCH_2CH_2CH_2Ar$), 2.07 (3H, s, $CH_3COO$), 2.58-2.73 (4H, m, $NHCH_2CH_2CH_2Ar$), 4.81 (1H, q, J=6.7 Hz, $CHCH_3$), 6.81 (2H, br s, $^+NH_2$) 7.26 (1H, d, J=7.6 Hz, $CF_3$-phenyl 6-H), 7.32 (1H, t, J=7.6 Hz, $CF_3$-phenyl 5-H), 7.36 (1H, s, $CF_3$-phenyl 2-H), 7.41 (1H, d, J=7.6 Hz, $CF_3$-phenyl 4-H), 7.48-7.56 (3H, complex signal, naphthyl 3-H, 6-H, 7-H), 7.69 (1H, d, J=7.2 Hz, naphthyl 4-H), 7.79 (1H, d, J=8.0 Hz, naphthyl 5-H), 7.89 (1H, dm, J=7.6 Hz, naphthyl 8-H), 8.13 (1H, d, J=8.0 Hz, naphthyl 2-H) (see FIG. 5); $^{13}$C NMR ($CDCl_3$, 100.6 MHz): 22.1 ($CH_3COO$), 22.7 ($CHCH_3$), 29.6 ($NHCH_2CH_2CH_2Ar$), 32.9 ($NHCH_2CH_2Ar$), 46.0 ($NHCH_2CH_2CH_2Ar$), 53.0 ($CHCH_3$), 122.3 (naphthyl C8) 122.8 (q, J=3.9 Hz, $CF_3$-phenyl C4), 125.0 (q, J=3.8 Hz, $CF_3$-phenyl C2), 123.3, 125.71, 125.72 and 126.4 (naphthyl C2, C3, C6 and C7), 125.5 (part of q, $CF_3$, rest of signal obscured), 128.2 ($CF_3$-phenyl C5), 128.7 (naphthyl C5), 129.1 (naphthyl C4), 130.6 (q, J=31.8 Hz, $CF_3$-phenyl C3), 131.1 (naphthyl C8a), 131.6 ($CF_3$-phenyl C6), 133.9 and 137.2 (naphthyl C4a and naphthyl C1), 142.1 ($CF_3$-phenyl C1), 176.9 ($CH_3COO$); MS (direct infusion, electrospray +), m/z (%): 359 (54), 358 ([M+H]$^+$, 100), 204 (41), 156 (53), 155 (84); Elemental analysis: $C_{22}H_{22}F_3N \cdot CH_3COOH$ (417.47): C 69.05%, H 6.28%, N 3.36%, F 13.65%. Found: C 68.73%, H 6.34%, N 3.28%, F 13.67%; XRD: 2θ (± 0.2°) 7.9, 10.6, 11.7, 12.0, 12.8, 13.1, 15.8, 16.0, 17.0, 18.0, 19.8, 20.5, 21.3, 21.7, 22.5, 23.1, 24.0, 24.7, 26.0, 26.2, 27.7, 29.7, 31.7, 33.8, 34.3, 35.7 (see FIG. 7).

Example 4

Preparation of Cinacalcet Hydrochloride from Cinacalcet Acetate

To a stirred solution of 14.97 g (35.90 mmol) cinacalcet acetate, prepared according to Example 3, and 69 mL isobutyl acetate at room temperature, 49.71 g (90.00 mmol) of 10.58% w/w NaCl aqueous solution were added dropwise. The formation of a thick white suspension was observed. The mixture was stirred at room temperature overnight and then cooled to 5-10° C. n-Heptane (54 mL) was then added dropwise, and the suspension was stirred at 5-10° C. for 1 hour. The solid was filtered and washed with 15 mL of isobutyl acetate to give 17.69 g of material (LOD: 26.54%, yield: 91.9%).

The wet material (16.60 g) was stirred with 55 mL of water for 1 hour at room temperature. The suspension was then cooled to 5-10° C. and stirred for 30 minutes. The suspension was filtered and washed with 17 mL of water to give 12.45 g of material (LOD: 4.45%, yield: 97.6%).

The wet material (11.52 g) was dissolved in 44 mL of ethanol and filtered to remove insoluble particles. About 70% of the solvent was distilled under vacuum and the remainder was displaced using two 44 mL portions of isobutyl acetate.

Isobutyl acetate (66 mL) was added to the resulting suspension, and the mixture was heated until dissolution occurred. The solution was then allowed to cool to 85° C., and 27.5 mL of n-heptane was added dropwise. The resulting suspension was cooled to 0-5° C. and stirred at this temperature for 1 hour. The solid was filtered and washed with 10 mL of isobutyl acetate to give 16.69 g of material (LOD: 35.82%, yield: 97.3%).

Finally, 15.59 g of wet material and 60 mL of isobutyl acetate were heated until dissolution occurred. The solution was cooled to 0-5° C. and stirred for 1 hour. The solid was filtered and washed with 10 mL of isobutyl acetate. The product was dried at 60° C. for 4 hours under vacuum to yield 9.68 g of white solid (yield: 96.7%). Overall yield: 84.4%.

Figure 6:
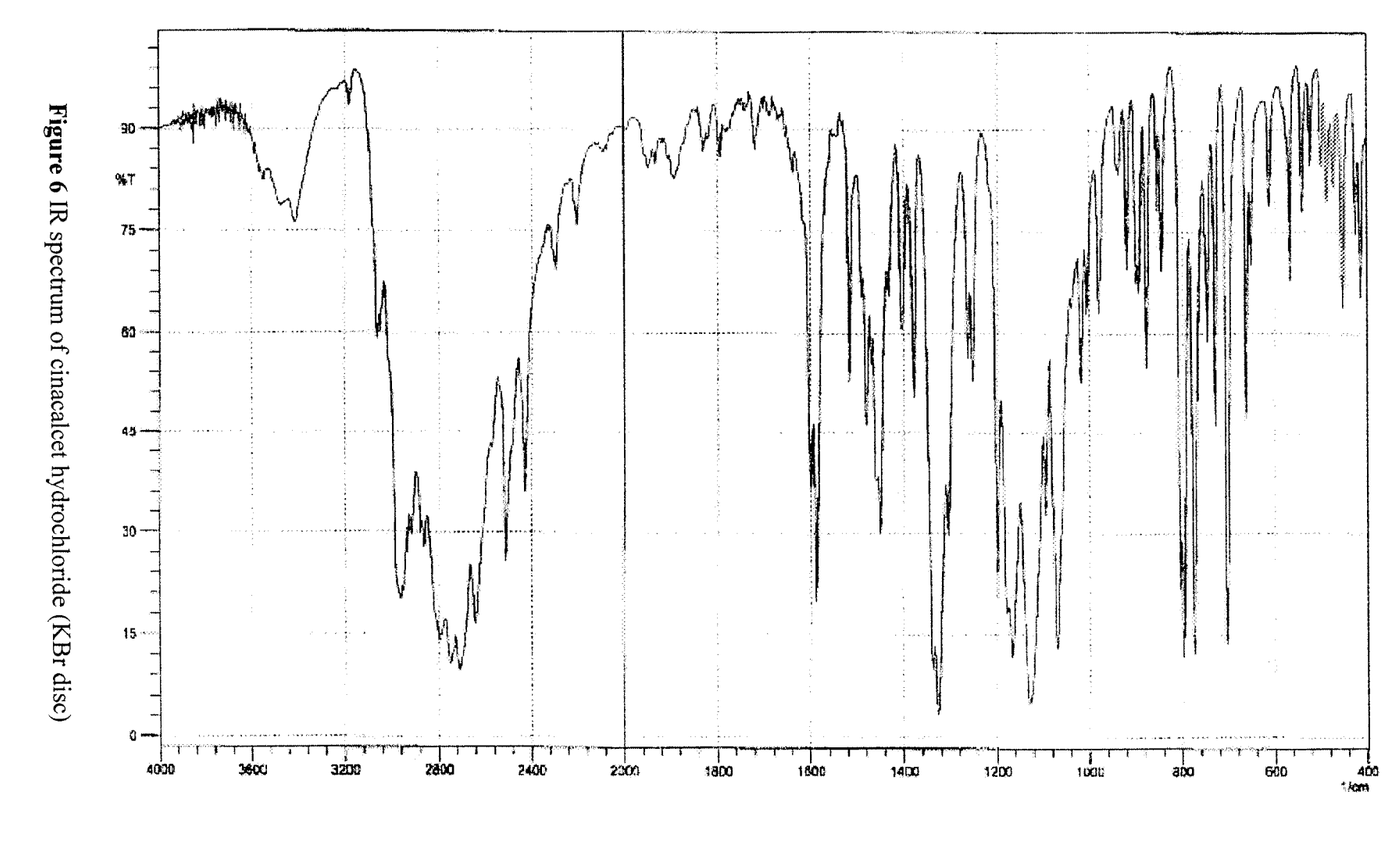
FIG. 6 illustrates the Infra Red spectrum of cinacalcet hydrochloride (KBr disc)

The following analyses of the dry solid were made: Potentiometric assay: 100.2%, Cl content: 8.97% (theoretical content: 9.01%); Optical rotation $[\alpha]_D^{20}$: −29.1° (C=2, MeOH); Melting range: 180.4-180.9° C.; HPLC: 99.98% (% area); IR according to FIG. 6.

Example 5

Preparation of Cinacalcet Hydrochloride from Cinacalcet Acetate

To a stirred solution of 15.00 g (35.93 mmol) cinacalcet acetate, prepared according to Example 3, and 69 mL isobutyl acetate at 5-10° C., 21.76 g (47.79 mmol) of 8% w/w HCl aqueous solution were added dropwise. The formation of a thick white suspension was observed. The mixture was stirred at 5-10° C. for 30 min. 54 mL of n-heptane were then added dropwise, and the suspension was stirred at 5-10° C. for 1 hour. The solid was filtered and washed with 15 mL of isobutyl acetate to give 20.50 g of material (LOD: 34.09%, yield: 95.5%).

The wet material (18.55 g) was stirred with 55 mL of water for 1 hour at room temperature. The suspension was then cooled down to 5-10° C. and stirred for 30 min. The suspension was filtered and washed with 15 mL of water to give 15.83 g of material (LOD: 25.55%, yield: 96.4%).

The wet material (14.86 g) was dissolved in 44 mL of ethanol and filtered to remove insoluble particles. About 70% of the solvent was distilled under vacuum, and the remainder was displaced using two 44 mL portions of isobutyl acetate.

Isobutyl acetate (66 mL) was added to the resulting suspension, and the mixture was heated up until dissolution occurred. The solution was then allowed to cool down to 85° C., and 27.5 mL of n-heptane were added dropwise. The resulting suspension was cooled down to 0-5° C. and stirred at this temperature for 1 hour. The solid was filtered and washed with 10 mL of isobutyl acetate to give 9.00 g of material (LOD: 0.53%, yield: 80.9%).

Finally 8.11 g of wet material and 54 mL of isobutyl acetate were heated until dissolution occurred. The solution was cooled down to 0-5° C. and stirred for 1 hour. The solid was filtered and washed with 10 mL of isobutyl acetate. The product was dried at 60° C. for 4 hours under vacuum to give 7.88 g of white solid (yield: 97.7%). Overall yield: 72.7% The following analyses of the dry solid were made: Potentiometric assay: 100.1%, Cl content: 8.99% (theoretical content: 9.01%); Melting range: 180.7-180.9° C.; HPLC: 99.97% (% area). IR (KBr), ν (cm$^{-1}$): 3063, 3051, 2962, 2864, 2797, 2750, 2712, 2642, 2513 and 2428 (C—H st and $^+$NH st), 1599, 1587, 1518 (Ar C—C st), 1479, 1450, 1404, 1379, 1339, 1327, 1304, 1261, 1252, 1200, 1178, 1167, 1128, 1094, 1070, 1018, 1007, 980, 920, 901, 895, 878, 845, 804, 797, 773, 746, 729, 704, 663 (see FIG. 6).

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. A process for preparing cinacalcet hydrochloride, the process comprising:
   i. providing a cinacalcet carboxylate salt; and
   ii. converting the cinacalcet carboxylate salt into cinacalcet hydrochloride via an anion exchange reaction.

2. The process of claim 1, wherein the cinacalcet carboxylate salt is a cinacalcet $C_{1-5}$ carboxylate salt.

3. The process of claim 2, wherein the cinacalcet $C_{1-5}$ carboxylate salt is cinacalcet acetate.

4. The process of claim 1, wherein the step of providing a cinacalcet carboxylate salt comprises:
   i. contacting cinacalcet free base with a carboxylic acid in a mixture of an organic solvent and water;
   ii. removing the water from the mixture; and
   iii. optionally, isolating cinacalcet carhoxylate from the mixture.

5. The process of claim 4, wherein the carboxylic acid is a $C_{1-5}$ carboxylic acid.

6. The process of claim 5, wherein the carboxylic acid is acetic acid.

7. The process of claim 1, wherein the step of converting the cinacalcet carboxylate salt into cinacalcet hydrochloride via, an anion exchange reaction comprises:
   i. contacting the cinacalcet carboxylate salt with a compound donor of chloride ions in a mixture of an organic solvent and water;
   ii. isolating cinacalcet hydrochloride from the mixture; and
   iii. optionally, purifying said cinacalcet hydrochloride.

8. The process of claim 7 wherein the compound donor of chloride ions is at least one of hydrogen chloride, hydrochloric acid, alkali metal chloride, and ammonium chloride.

9. A process for preparing cinacalcet acetate, the process comprising:
   i. contacting cinacalcet free base with acetic acid in a mixture of an organic solvent and water;
   ii. removing the water from the mixture; and iii. isolating cinacalcet acetate from the Mixture.

10. The process of claim 4, wherein the organic solvent is at least one of an alcohol solvent and an ester solvent.

11. The process of claim 10 wherein the alcohol solvent is a $C_{1-5}$ alcohol solvent.

12. The process of claim 10, wherein the ester solvent is an acetate ester solvent.

13. The process of claim 7, wherein the organic solvent is at least one of an alcohol solvent and an ester solvent.

14. The process of claim 13, wherein the alcohol solvent is a $C_{1-5}$ alcohol solvent.

15. The process of claim 13, wherein the ester solvent is an acetate ester solvent.

16. The process of claim 9, wherein the organic solvent is at least one of an alcohol solvent and an ester solvent.

17. The process of claim 16, wherein the alcohol solvent is a $C_{1-5}$ alcohol solvent.

18. The process of claim 16, wherein the ester solvent is an acetate ester solvent.

19. The process of claim 8, wherein the compound donor of chloride ions is at least one of hydrochloric acid and sodium chloride.

20. The process of claim 11, wherein the $C_{1-5}$ alcohol solvent is isopropanol.

21. The process of claim 12, wherein the acetate ester solvent is isobutyl acetate.

22. The process of claim 14, wherein the $C_{1-5}$ alcohol solvent is isopropanol.

23. The process of claim 15, wherein the acetate ester solvent is isobutyl acetate.

24. The process of claim 17, wherein the $C_{1-5}$ alcohol solvent is isopropanol.

25. The process of claim 18 wherein the acetate ester solvent is isobutyl acetate.

* * * * *